United States Patent [19]

Bhise et al.

[11] 4,437,939
[45] Mar. 20, 1984

[54] PROCESS FOR SEPARATING ETHYLENE OXIDE FROM AQUEOUS SOLUTIONS

[75] Inventors: Vijay S. Bhise, Bloomfield, N.J.; Robert Hoch, Ridgewood, N.Y.

[73] Assignee: The Halcon SD Group, Inc., New York, N.Y.

[21] Appl. No.: 321,966

[22] Filed: Nov. 16, 1981

Related U.S. Application Data

[63] Continuation-in-part of Ser. No. 284,153, Jul. 17, 1981.

[51] Int. Cl.³ .................... B01D 3/34; C07D 301/32
[52] U.S. Cl. ......................................... 203/14; 203/43; 203/49; 203/67; 203/68; 203/70; 549/541
[58] Field of Search ................... 260/348.37; 203/43, 203/42, 14, 91, 49, 70, 67, 68; 422/256–260; 196/14.52; 210/634, 511; 202/169

[56] References Cited

U.S. PATENT DOCUMENTS

| | | | |
|---|---|---|---|
| 2,771,473 | 11/1956 | Courter | 260/348.37 |
| 3,265,593 | 8/1966 | Leis et al. | 203/64 |
| 3,418,338 | 12/1968 | Gilman et al. | 260/348.37 |
| 3,964,980 | 6/1976 | Ozero | 203/42 |
| 3,969,196 | 7/1976 | Zosel | 203/49 |
| 4,349,415 | 9/1982 | De Filippi et al. | 203/14 |

FOREIGN PATENT DOCUMENTS 2059787 4/1981 United Kingdom .

*Primary Examiner*—Wilbur L. Bascoomb, Jr.
*Attorney, Agent, or Firm*—William C. Long; Riggs T. Stewart; Harold N. Wells

[57] ABSTRACT

Ethylene oxide is extracted from aqueous solutions by carbon dioxide under (near) super-critical conditions and thereafter recovered by distillation at sub-critical conditions. Improved distillation is obtained by adding to the carbon dixoide a gas (or gases) which adjust the critical temperature of the gas mixture of the top of the distillation column within the range of about 32° C. to about 75° C. Preferred gases are the saturated hydrocarbons, particularly propane, n-butane, isobutane and pentane.

6 Claims, 2 Drawing Figures

PROCESS FOR SEPARATING ETHYLENE OXIDE FROM AQUEOUS SOLUTIONS

REFERENCE TO RELATED APPLICATIONS

This application is a continuation-in-part of co-pending application Ser. No. 284,153, filed July 17, 1981.

PRIOR ART

The invention relates to the recovery of ethylene oxide from aqueous solutions. The use of carbon dioxide under near-critical or super-critical conditions to selectively extract ethylene oxide from the dilute aqueous solutions produced by scrubbing with water the effluent from ethylene oxidation reactors was disclosed generally in our U.S. patent application referenced above. It was indicated there that other gases could be introduced into the separation process to assist in condensing carbon dioxide. We have now found that the types of gases and the conditions under which they are employed are limited by the interactions with the process, as will be seen in the description which follows.

SUMMARY OF THE INVENTION

Ethylene oxide produced by the vapor-phase oxidation of ethylene over a catalyst is recovered by absorption in water to produce dilute aqueous solutions of ethylene oxide. These solutions may be separated and the ethylene oxide recovered by extracting ethylene oxide with (near) super-critical carbon dioxide, followed by sub-critical distillation. Such distillations are improved according to the invention by adding to the carbon dioxide gas (or gases) so that the critical temperature of the carbon dioxide-ethylene oxide-added gas mixture at the top of the distillation column is between about 32° C. and about 75° C. The critical temperature of the gas will be generally between about 35° and 150° C. and it will be chemically unreactive with the remaining components of the process and either have no effect on the ethylene oxidation reaction or be removable from the recirculating aqueous absorbent. A variety of gases may be used, including paraffins, cycloparaffins, olefins, and halogenated paraffins. Preferred gases are one or more members of the group consisting of saturated hydrocarbons and saturated hydrocarbons that are halogenated in one or more positions. Propane, n-butane, isobutane, and pentane are particularly advantageous. Suitable amounts will range from 0.01 to 0.5 mols of gas per mol of carbon dioxide at the top of the distillation column. For n-butane 0.05-0.15 mol per mol of carbon dioxide is preferred, for propane 0.1-0.3 mol per mol of carbon dioxide, and for n-pentane 0.01-1 mol per mol of carbon dioxide. A preferred refrigerant 13B1 (DuPont) would be employed in amounts of about 0.1-0.3 mol per mol of carbon dioxide.

DESCRIPTION OF THE PREFERRED EMBODIMENTS

Figure 1:
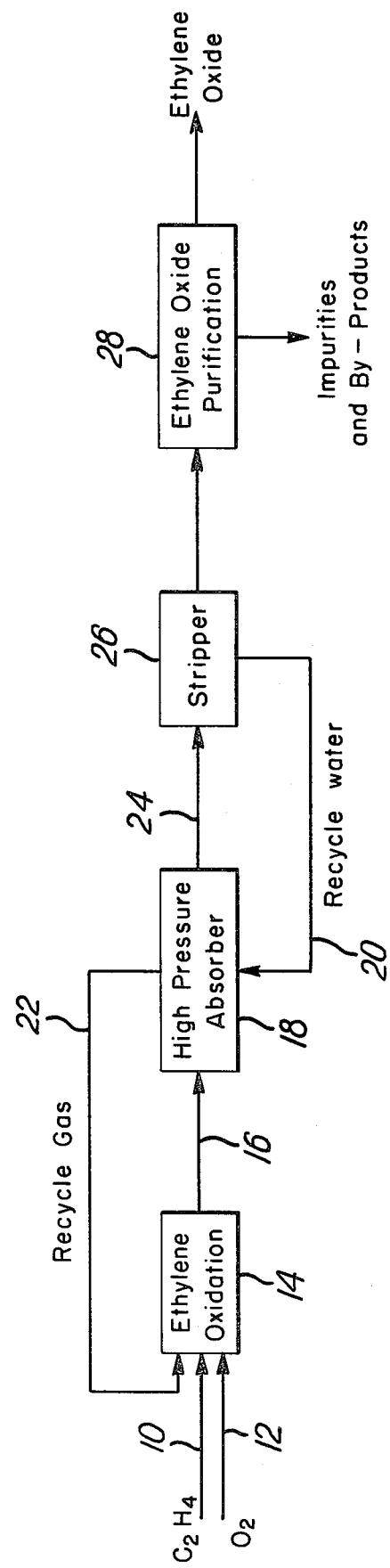
FIG. 1 is a block diagram illustrating the process for catalytic oxidation of ethylene to ethylene oxide and its recovery.

The conventional ethylene oxide process is illustrated schematically in FIG. 1. Ethylene (10) and oxygen (12) are fed to a catalytic oxidation reactor (14) employing a supported silver catalyst disposed inside tubes, which are surrounded by a heat transfer fluid used to remove the heat of reaction. Only a fraction of the ethylene is converted to ethylene oxide in each pass through the reactor and consequently a significant amount of ethylene is usually recycled, along with diluent gases, such as nitrogen or methane, to the reactor. Gases leaving the reactor via line 16 at about 10–40 $kg/cm^2$ gauge and 200°–400° C. are cooled and passed to a high pressure absorber (18) where they meet a recycling water stream (20) and the ethylene oxide is absorbed, along with carbon dioxide and various impurities produced in the oxidation reactor. The gases which are not absorbed are separated from the aqueous ethylene oxide solution and recycled via line 22 to the reactor (14). The ethylene oxide-rich solution is sent via line 34 to a stripper (26) where ethylene oxide is separated and the lean water recycled via line 20 to the high pressure absorber (18). After this, the gaseous ethylene oxide may be absorbed again in a suitable solvent such as water or ethylene carbonate and separated from various impurities, by known methods which are shown in this figure generally as a purification step (28). The final product may be substantially pure ethylene oxide as indicated, or alternatively, a mixture of ethylene oxide and carbon dioxide could be produced, which is useful for preparation of ethylene carbonate.

Figure 2:
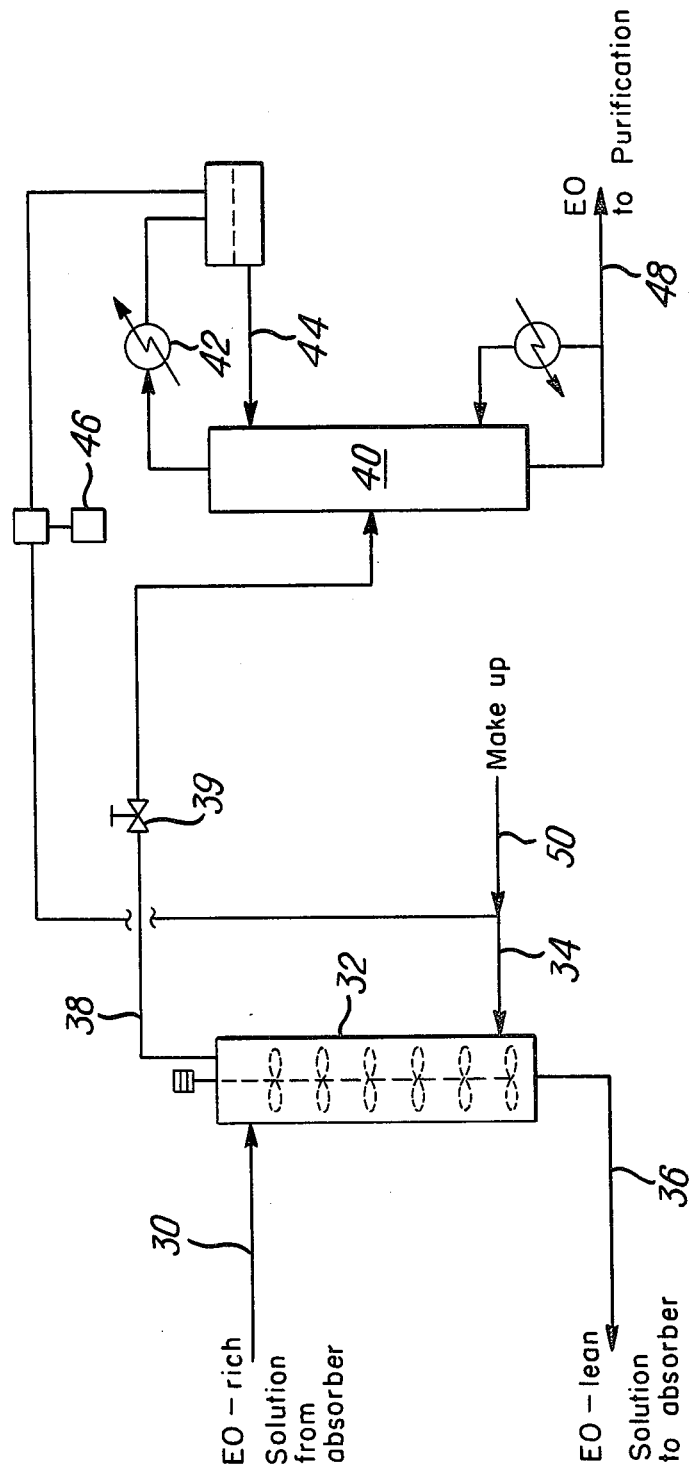
FIG. 2 shows the recovery of ethylene oxide from high pressure aqueous solutions using (near) super-critical carbon dioxide.

The invention is illustrated with respect to the flow sheet of FIG. 2, in which the aqueous stream 24 of FIG. 1 is shown as stream 30. This is an aqueous solution containing about 0.1–10 mol % ethylene oxide at about 10–40 $kg/cm^2$ gauge and 50°–100° C. The large amount of water must be separated from the ethylene oxide and in conventional processing substantial energy costs are incurred. However, by employing carbon dioxide at (near) super-critical conditions ethylene oxide can be extracted more efficiently. One method, shown in FIG. 2, is to employ a staged mixer 32 into which carbon dioxide is introduced via line 34 and flows countercurrently to the aqueous ethylene oxide solution. As will be understood by those skilled in the art, the number of mixing stages and the amount of carbon dioxide may be varied to produce the optimum conditions for extraction of the desired amount of ethylene oxide, which is the net production of ethylene oxide in the oxidation reactor (14 in FIG. 1). A small amount of water will also be absorbed since it is present in very large amounts relative to ethylene oxide, but it is a feature of this process that carbon dioxide can be used to selectively extract ethylene oxide from large amounts of water. Organic by-products, of the ethylene oxidation process such as aldehydes, also may be absorbed by the carbon dioxide. Some of the carbon dioxide will be absorbed by the water and leave column 32 via stream 36. The ethylene oxide-loaded carbon dioxide is then passed to a distillation column 40, which operates at sub-critical conditions selected to permit good separation of carbon dioxide from ethylene oxide, while minimizing the cost of compressing the recycled carbon dioxide via compressor 46. The pressure in column 40 will be about 30–75 $kg/cm^2$ gauge, but the operating pressure should be near the critical value of carbon dioxide to take advantage of the reduced latent heat of vaporization, as well as to minimize compression of carbon dioxide. The energy requirements also can be reduced further if pressure letdown valve 39 is replaced by an expander to recover power. In a typical embodiment where pure carbon dioxide is used the operating pressure in extraction column 32 would be about 75–300 kg/cm² gauge and in distillati columnon 40, about 30–75 kg/cm² gauge. Since the overhead condenser 42 operates with a nearly pure stream of carbon dioxide, the temperature must be below the critical temperature for carbon dioxide, namely, 31° C. Such temperatures are difficult to achieve with cooling water under warm ambient conditions and, consequently, a gas (or gases) having a higher critical temperature than carbon dioxide is added to raise the condensing temperature and avoid the need for expensive refrigeration. While the broad concept suggests that a wide selection of gases would be suitable, in fact it has been found that the choices are limited, as will be seen.

A gas added to the carbon dioxide-water-ethylene oxide system (neglecting for this discussion the effect of by-products of ethylene oxidation) should have the effect of raising both the critical temperature in the distillation column overhead equipment and the temperature at which carbon dioxide is condensed, thus achieving the desired result. Ideally, the gas only affects the separation of ethylene oxide from the bulk of the carbon dioxide. However, any gas which is added is not confined solely to the distillation column 40, but will be returned with the carbon dioxide to the extraction column 32. From there, some will find its way into the ethylene oxidation along with some carbon dioxide via stream 36. Some of the gas will also be present in the ethylene oxide-carbon dioxide mixture leaving the distillation column 40 via line 48. It is preferred that the added gas have a greater volatility than ethylene oxide so that it can be recovered with the carbon dioxide by distillation. We have found that only a limited number of gases can be satisfactorily used in this process when all factors are considered.

The added gas should be inert. Not only should it not react with ethylene oxide or the organic by-products, but it should not adversely affect the oxidation of ethylene to ethylene oxide. Therefore, the gas should be limited to relatively unreactive materials, such as paraffins, halogenated hydrocarbons, and those inert compounds generally referred to as refrigerants. Among these general classes, propane, n-butane, isobutane, pentane and halogenated refrigerants such as DuPont's 12, 13B1, 22, 32, 115, 142b, 152a, 245, C318, 500, 502, and 504 are particularly preferred for this service. Generally, even these relatively unreactive materials cannot be accepted in large amount in the ethylene oxidation reaction and, thus, the stream 36 would be processed to reduce the amount of the added gas in the usual case. This may be done by heating and flashing to a lower pressure, steam stripping or other techniques familiar to those skilled in the art.

Although it would appear at first that any inert gas would be useful if its critical temperature is higher than 31° C. and that the higher the temperature the better, it has been found that high molecular weight gases with their higher critical temperatures are not suitable since they must be in the overhead equipment to raise the condensing temperature and the higher molecular weight gases tend to be rejected from the distillation column bottoms via line 48. The heavier gases cannot be as readily vaporized and taken overhead in the distillation column, because the column bottom temperature has been set at a maximum of about 50° C., since undesirable side-reactions may become significant above that temperature. It will be expected by those skilled in the art that since the added gases will be less volatile than carbon dioxide, the operating pressure of the distillation column 40 would be lowered since the bottoms temperature is limited. Lowering the pressure of the distillation column is undesirable, since it directionally reduces the condensing temperature and counters the benefits of adding the gas, and also increasing the cost of recycling carbon dioxide to the extractor 32. However, since mixtures of carbon dioxide with n-butane and particularly pentane exhibit positive deviations from ideal behavior, the pressure of the column is not significantly reduced. Satisfying these requirements, it has been found that the added gas should have a critical temperature between about 35° C. and about 250° C. and should be inert. Surprisingly then, there are actually only a relatively few gases which can be used.

As previously mentioned, various gases such as paraffins, cycloparaffins, halogenated paraffins, and olefins may be used. Paraffins are especially useful, including propane, n-butane, isobutane, and pentane. Of these n-butane, is particularly preferred. Other gases which are preferred include the refrigerants listed earlier. The amount of the gas(es) selected will fall generally within the range of about 0.05–0.15 mol/mol of carbon dioxide. It is considered undesirable to use more gas than is needed to provide the preferred condensing temperature for the carbon dioxide-ethylene oxide-added gas mixture at the top of the distillation column 40. Excessive amounts of the added gas(es) will increase costs of operating associated facilities which must handle the gas.

The following example will compare the processing scheme of FIG. 2 when pure carbon dioxide is used and when propane, n-butane, pentane, and refrigerant 13B1 are included.

EXAMPLE 1

Comparative Example

An aqueous stream containing 0.8 mol percent ethylene oxide (neglecting minor amounts of by-products) is fed to extraction column 32 via line 30 at a rate of 1000 mol/hr. A stream of carbon dioxide is fed via line 34 at a rate of 438.9 mol/hr. The streams are contacted in 8 stages at a temperature of 45° C. and a pressure of 112.5 kg/cm² gauge. The stripped water leaving column 32 via line 36 has a flow rate of 1034 mol/hr. It contains only 1% of the ethylene oxide fed to the column and has absorbed about 9–10% of the carbon dioxide fed. This stream is heated to 50°–150° C. and then flashed to a pressure of about 1–50 kg/cm² to remove the carbon dioxide, which can be recompressed and returned to the extraction column. The ethylene oxide-laden carbon dioxide is reduced in pressure and passed via line 38 to distillation column 40. This column is operated at about 66 kg/cm². The overhead condensing temperature is 25° C., thus refrigeration generally will be needed. About 95.7% of the carbon dioxide is taken as an overhead product and returned via compressor 46 and line 34 to column 32. The remainder leaves via line 48, along with substantially all of the ethylene oxide fed. That stream also contains about 0.6 mol % water absorbed in column 32 by the carbon dioxide. The temperature is about 50° C. Carbon dioxide losses are replaced via line 50.

EXAMPLE 2

Propane Added

Again, stream 30 has the same flow rate and composition as in Example 1. The carbon dioxide stream 34 has a flow rate of 436 mol/hr and contains about 19.4 mol % propane. The extraction is carried out at the same conditions as Example 1. The stripped water leaves at a rate 1031 mol/hr and contains about 9–10% of the carbon dioxide fed and about 6–7% of the propane. This stream (36) is heated to about 50°–150° C. and than flashed to a pressure of about 1–50 kg/cm$^2$ gauge to remove the carbon dioxide and propane before the solution is used to absorb ethylene oxide again. Distillation column 40 is operated at about 43.6 kg/cm$^2$ gauge with an overhead temperature of 35° C., permitting the use of cooling water rather than refrigeration for condensing the column reflux. The bottom temperature again is 50° C. About 95.7% of the carbon dioxide is taken overhead and returned to the extraction column 32, along with about 53.5% of the propane fed to distillation column 40. The remainder of the propane leaves via line 48 in a stream containing about 4.3% of the carbon dioxide fed, all of the ethylene oxide and having about 0.3 mol % water. Carbon dioxide and propane losses are replaced via line 50.

EXAMPLE 3

N-butane Added

Stream 30 has the same flow rate and composition as in Example 1. The carbon dioxide stream 34 has a flow rate of 437 mol/hr and contains about 9.6 mol % n-butane. The extraction is carried out at the same conditions as Example 1. The stripped water leaves at a rate of 1032 mol/hr and contains about 9–10% of the carbon dioxide fed and about 5–6% of the n-butane. Again this stream (36) is processed to remove carbon dioxide and n-butane before reuse of the aqueous solution. Distillation column 40 is operated at about 54 kg/cm$^2$ gauge with an overhead temperature of 32° C., permitting the use of cooling water rather than refrigeration for condensing the column reflux. The bottom temperature again is 50° C. About 95.7% of the carbon dioxide is taken overhead and returned to the extraction column 32, along with about 63% of the n-butane fed to the distillation column 40. The remainder of the n-butane leaves via line 48 in a stream containing about 4.3% of the carbon dioxide fed, all of the ethylene oxide and having about 0.5 mol % water. Carbon dioxide and n-butane losses are replaced via line 50.

EXAMPLE 4

N-pentane Added

Again, stream 30 has the same flow rate and composition as in Example 1. The carbon dioxide stream 34 has a flow rate of 441 mol/hr and contains about 5.4 mol % n-pentane. The extraction is carried out at the same conditions as Example 1. The stripped water leaves at a rate 1036 mol/hr and contains about 9–10% of the carbon dioxide fed and about 16–17% of the n-pentane. As in Examples 2 and 3, this stream (36) is processed to remove carbon dioxide and n-pentane prior to reuse. Distillation column 40 is operated at about 64 kg/cm$^2$ gauge with an overhead temperature of 35° C., permitting the use of cooling water rather than refrigeration for condensing the column reflux. The bottom temperature again is 50° C. About 95.8% of the carbon dioxide is taken overhead and returned to the extraction column 32, along with about 84% of the n-pentane fed to distillation column 40. The remainder of the n-pentane leaves via line 48 in a stream containing about 4.3% of the carbon dioxide fed, all of the ethylene oxide and having about 0.6 mol % water. Carbon dioxide and n-pentane losses replaced via line 50.

EXAMPLE 5

Refrigerant Added

As before, stream 30 has the same flow rate and composition as in Example 1. The carbon dioxide stream 34 has a flow rate of 436 mol/hr and contains about 19.4% DuPont refrigerant 13B1 (an equivalent could also be used). The extraction conditions of Example 1 still pertain. Stripped water leaves at a rate of 1035 mol/hr and contains about 9–10% of the carbon dioxide fed and about 6–7% of the 13B1. This stream (36) is processed to remove carbon dioxide and 13B1 before the stripped water is reused to absorb ethylene oxide. Distillation column 40 is operated at about 36.6 kg/cm$^2$ gauge with an overhead temperature of 35° C., permitting the use of cooling water rather than refrigeration for condensing the column reflux. The bottom temperature is 50° C., as before. About 95.7% of the carbon dioxide is taken overhead and returned to the extraction column 40. The rest of the 13B1 refrigerant is contained in stream 48, which contains about 4.3 of the carbon dioxide fed, all of the ethylene oxide and has about 0.2 mol % water. Carbon dioxide and 13B1 losses are replaced via line 50.

While the carbon dioxide compression costs are nearly the same, Example 1 without an added gas, is more costly since refrigeration is required instead of much less expensive cooling water. Thus, the process of the invention has a significant advantage.

What is claimed is:

1. In a process for recovering ethylene oxide from aqueous solutions wherein carbon dioxide at near-critical or super-critical conditions extracts ethylene oxide and thereafter the extracted ethylene oxide is separated from the carbon dioxide by distillation at sub-critical conditions, the improvement comprising adding an amount of a gas or gases to said carbon dioxide sufficient to provide a critical temperature for the carbon dioxide-ethylene oxide-added gas mixture at the top of said distillation column between 32° C. and 75° C.

2. A process of claim 1 wherein said added gas is at least one member selected from the group consisting of propane, n-butane, isobutane, pentane, and halogenated refrigerants and the amount added is about 0.01–0.5 mols per mols of carbon dioxide of the top of said distillation column.

3. A process of claim 2 wherein said added gas is n-butane and the amount added is about 0.05–0.15 mols per mol of carbon dioxide at the top of said distillation column.

4. A process of claim 2 wherein said added gas is propane and the amount added is about 0.1–0.3 mols per mol of carbon dioxide at the top of said distillation column.

5. A process of claim 2 wherein said added gas is n-pentane and the amount added is about 0.01–0.1 mols per mol of carbon dioxide at the top of said distillation column.

6. A process of claim 2 wherein said added gas is a halogenated refrigerant and the amount added is about 0.1–0.3 mols per mol of carbon dioxide at the top of said distillation column.

* * * * *

UNITED STATES PATENT AND TRADEMARK OFFICE
CERTIFICATE OF CORRECTION

PATENT NO. : 4,437,939

DATED : March 20, 1984

INVENTOR(S) : Vijay S. Bhise and Robert Hoch

It is certified that error appears in the above-identified patent and that said Letters Patent are hereby corrected as shown below:

On the title page;

Abstract, line 5: Change "dixoide" to -- dioxide --;

Column 3, line 4: Change "distillati columnon" to -- distillation column --;
         line 5: Change "42-operates" to -- 42 operates --;
         line 68: Change "significent" to -- significant --;

Column 5, line 11: Change "than" to -- then --;

Column 6, line 25: Change "column 40" to -- column 32 --;
         line 27: Change "4.3 of" to -- 4.3% of --.

Signed and Sealed this

First Day of October 1985

[SEAL]

Attest:

DONALD J. QUIGG

Attesting Officer

Commissioner of Patents and Trademarks—Designate